United States Patent [19]

Park et al.

[11] Patent Number: 5,230,899
[45] Date of Patent: Jul. 27, 1993

[54] METHODS AND COMPOSITIONS FOR MAKING LIPOSOMES

[75] Inventors: John Y. Park, Santa Ana; Shurl A. Thompson, El Toro, both of Calif.

[73] Assignee: SmithKline Beecham Corporation, Philadelphia, Pa.

[21] Appl. No.: 714,984

[22] Filed: Jun. 14, 1991

Related U.S. Application Data

[63] Continuation of Ser. No. 418,924, Oct. 6, 1989, abandoned, which is a continuation of Ser. No. 3,101, Jan. 14, 1987, abandoned, which is a continuation-in-part of Ser. No. 763,484, Aug. 7, 1985, abandoned.

[51] Int. Cl.$^5$ .................. A61K 9/127; B01J 13/02
[52] U.S. Cl. .................... 424/450; 264/4.1; 264/4.3; 424/1.1; 428/402.2; 436/829; 514/944
[58] Field of Search .............. 264/4.1, 4.6; 428/402.2; 424/450; 436/829; 260/404, 404.5; 554/79, 80; 514/944

[56] References Cited

U.S. PATENT DOCUMENTS

| | | | |
|---|---|---|---|
| 3,957,971 | 5/1976 | Oleniacz | 424/70 |
| 4,145,410 | 3/1979 | Sears | 264/4.1 X |
| 4,235,871 | 11/1980 | Papahadjopoulos et al. | 424/450 X |
| 4,308,166 | 12/1981 | Marchetti et al. | 264/4.6 X |
| 4,508,703 | 4/1985 | Redziniak et al. | 424/450 |
| 4,789,633 | 12/1988 | Huang et al. | 424/450 X |

FOREIGN PATENT DOCUMENTS

| | | | |
|---|---|---|---|
| 0087993 | 2/1982 | European Pat. Off. | |
| 0130577 | 6/1983 | European Pat. Off. | |
| 3301951 | 7/1984 | Fed. Rep. of Germany | 264/4.1 |
| 2135268 | 8/1984 | United Kingdom | 424/450 |

*Primary Examiner*—Richard D. Lovering
*Attorney, Agent, or Firm*—James M. Kanagy; Stuart R. Suter; Edward T. Lentz

[57] ABSTRACT

Liposome-forming materials containing a long chain aliphatic or aromatic-based acid or amine, hydrating agents and discrete amounts of water form gels which are useful drug delivery systems and spontaneously form highly stable liposomes in aqueous solution having very high capture efficiency.

11 Claims, No Drawings

METHODS AND COMPOSITIONS FOR MAKING LIPOSOMES

This application is a continuation of U.S. Ser. No. 07/418,924 filed Oct. 6, 1989 now abandoned, which is a continuation U.S. Ser. No. 07/003101 filed Jan. 14, 1987, now abandoned, which was a continuation-in-part of U.S. Ser. No. 06/763,484 filed Aug. 7, 1985, now abandoned.

BACKGROUND

This invention relates to novel compositions which provide a new method for forming liposomes and can be used as drug delivery vehicles. More specifically, this invention relates to the use of hydrating agents, compounds with at least two ionizable groups, in conjunction with liposome-forming materials containing a long chain aliphatic or aromatic-based acid or amine to make a gel which spontaneously forms liposomes when diluted with an aqueous medium. This gel is also useful as a drug delivery vehicle.

GENERAL DESCRIPTION

Numerous processes and methods have been developed for making the different types and sizes of liposomes and for encapsulating active ingredient. Most of these methods have focused on the use of an organic solvent to ensure complete solubilization and uniform mixing of the phospholipids and fatty acids prior to dispersion in an aqueous system. A second development was the use of ultrasonic irradiation to disperse the phospholipid/fatty acid material.

For example Robinson, *Trans. Faraday Soc.*, 56:1260 (1960) and Papahadjopoulos, et al. [*Biochim. Biophys. Acta*, 135, 639 (1967)] describe formation of phospholipid dispersions from a two-phase ether/water system involving evaporation of the ether by bubbling nitrogen through the mixture. Similarly, chloroform has been used by Chowhan, et al., *Biochim. Biophys. Acta*, 266:320 (1972) to insure a complete and thorough mixing of the phospholipids prior to dispersion.

Ultrasonic dispersion, first described by D. Papahadjopoulos and N. Miller in *Biochim. Biophys. Acta*, 135:624 (1967) produces small unilamellar vesicles but the technique is limited because of low encapsulation efficiency.

Batzri and Korn [*Biochim. Biophys. Acta*, 198:1015 (1973] have used the technique of injecting the lipids in an organic phase (ethanol) into an aqueous solution. Ether was used by Deamer and Bangham in essentially the same technique [*Biochim. Biophys. Acta.* 443:619 (1976)].

Yet another technique involves a calcium-induced structural change in a lipid vesicle derived from or containing phosphatidylserine but is reported to have a relatively low encapsulation efficiency due to the method of reconstitution of the vesicle. See Papahadjopoulos, et al., *Biochim. Biophys. Acta*, 394:483 (1975) and H. Hauser, Trends in Pharm., *Science* 3, 274–77 (1982).

Several other patents set out methods for lipid vesicle formation of interest to this invention. U.S. Pat. No. 3,804,776 describes a method for producing oil and fat encapsulated amino acids for polypeptides by dispersing dry powders of the material in a molten mixture of the fat or oil and then pouring the mixture into water. The encapsulated material is contained within relatively large droplets of lipid. Such vesicles are not suitable for IV injection and are limited to use only for oral administration.

Entrapment of certain drugs in lipid vesicles by freezing the aqueous phospholipid dispersion of the drug and lipid is described in U.S. Pat. No. 4,016,100.

Papahadjapoulous and Szoka, in U.S. Pat. No. 4,235,871, disclose a method for making liposomes where the vesicle-forming material is dissolved in an organic solvent and then mixed with an aqueous solution containing the material to be encapsulated. An homogeneous water-in-oil emulsion is formed and the organic solvent is evaporated to give a gel-like mixture. This gel is then suspended in water to form the vesicles.

Another process of interest is disclosed in U.S. Pat. No. 3,932,657, which teaches the encapsulation of polyaminopolycarboxylic chelating agents, EDTA and TDPA. Yet another U.S. Pat. No. 4,217,344, issued to Vanlerberghe, et al., notes that certain additives can be combined with nonionic lipid compounds so as to modify the permeability and superficial charge of lipid vesicles. Among the several additives mentioned are polypeptides and proteins. Mackaness, et al. describe in U.S. Pat. No. 4,192,859, contrasts media containing liposomes as carriers. The list of contrast agent salts includes arginine salt, cystein salt, glycine salt, glycyl glycine salt, and N-methylglucosamine salts. These materials are characterized as aliphatic and alicyclic amines which can be used to prepare water soluble salts of the various contrast agents which may be employed in X-ray contrast agents.

An article in *Science,* March, 1984, by Janos Fendler makes reference to a number of synthetic surfactants which may be used in forming vesicles. Fendler references quaternary ammonium and carboxylate, sulfate, sulfonate and phosphate zwitterionic materials which are referenced to the following literature articles: J. H. Fendler, *Acc. Chem. Res.*, 13, 7 (1980); T. Kunitake and S. Shinkai, *Adv. Phis. Org. Chem.*, 17, 435 (1980); T. Kunitake, et. al., *J. Am. Chem. Soc.*, 103, 5401 (1981); J. H. Fuhrhop and J. Matthieu, *J. Chem. Soc. Chem. Commun.* p. 141 (1983); and W. Talmon, et. al., Science. 221, 1047 (1983).

It has been discovered that liposomes are spontaneously formed when phospholipids and/or long chain aliphatic or aromatic-based acids or amines, liposome forming materials, are dispersed in an aqueous solution containing a hydrating agent. More specifically, it has been discovered that liposomes are spontaneously formed when liposome forming materials are dispersed in an aqueous solution containing a such acids or amines and hydrating agent. Liposomes can be formed with these components by either forming a gel in which the three components are present with a discrete amount of water, then fully hydrating this gel where upon liposomes form, or secondly the hydrating agent may be added as part of the aqueous diluent, such addition effecting formation of liposomes with or without input of energy. Gels formed with this combination of components and water are also useful as drug delivery vehicles. Such gels may be used as a delivery system for the administration of medicaments via oral, parenteral, topical, intravenous, suppository routes or any other route of drug or chemical delivery.

Hydrating agents, for the purpose of this invention, is illustrated by arginine and similar amino acids which have at least one ionizable functionality at both the alpha and omega terminus of the molecule. These "hydrating" compounds will have either the same type of ionizable group on the molecule, both cationic, or both anionic, or have ionizable groups of opposite charge. It isn't required that the ionizable groups be on the alpha and omega carbons but such compounds represent the preferred embodiments of this invention.

In practical terms, liposomes formed using this invention are formulated as a "pre-liposome gel" referred to herein as a "gel" where a phospholipid and an aliphatic or aromatic-based acid or amine mixture capable of forming liposomes is mixed with an appropriate, concentrated aqueous solution of the hydrating compound. This gel, upon dispersion in an aqueous solution, efficiently and spontaneously forms liposomes without solvent evaporation, input of ultrasonic irradiation or any of the other means developed to insure proper formation of lipid vesicles, liposomes.

Liposomes made with hydrating agents are more stable than the ones produced by conventional methods, including those formed using organic solvents and ultrasonic energy. Liposome formulations having these hydrating agents suffer none of the solvent removal problems of the current technology nor are the liposomes beset by the non-uniform, destructive forces of ultrasonic irradiation inherent in the older methods.

Additionally, the pre-liposome gel can be dehydrated and stored for a substantial period of time and still be capable of spontaneously forming liposomes upon rehydration.

The pre-liposome gel is extraordinarily stable, stable enough to be autoclaved for sterilization. Furthermore, water-soluble or water-insoluble substances to be encapsulated can be added to the gel and will then be incorporated into the liposomes upon dispersion of the gel. This capability has the effect of greatly enhancing the encapsulation efficiency.

This gel can also be used as a drug delivery vehicle in and of itself without being converted into liposomes. When used a a vehicle for oral formulations, both delayed absorption and substantially increased bioavailability have been observed. Topical formulations based on this gel have shown salutary transdermal uptake properties.

In addition, it also has been discovered that the concentration of hydrating agent influences the size of the resulting liposomes in a predictable manner at a given pH. Correspondingly, varying the pH of the dispersing aqueous solution while holding the hydrating agent constant also influences the size of the liposomes produced in a predictable manner.

Thus, the present invention provides an easier, more convenient and predictable means for controlling vesicle size over methods previously available. This method also has no limitations on the concentrations of lipids in the preparation of liposomes.

SUMMARY OF THE INVENTION

This invention relates to a liposome product made by dispersing in an aqueous medium in a manner adequate to form liposomes, a composition comprising:
a. liposome-forming material containing a long chain aliphatic or aromatic-based acid or amine;
b. a hydrating agent of charge opposite to that of the acid or amine, which agent is present in a molar ratio of between 1:20 and 1:0.05 relative to the acid or amine;
c. water in an amount up to 300 moles relative to the solids; and
d. optionally, a material to be encapsulated.

Also, this invention covers a composition comprising:
a. liposome-forming material containing a long chain aliphatic or aromatic-based acid or amine;
b. a hydrating agent of charge opposite to that of the acid or amine, which agent is present in a molar ratio of between 1:20 and 1:0.05 relative to the acid or amine; and
c. water in an amount up to 300 moles relative to the solids.

In another aspect, this invention relates to a method for forming stable liposomes wherein the method comprises adding to liposome-forming materials where at least one of these materials is a long chain aliphatic or aromatic-based acid or amine an hydrating agent of charge opposite to that of the acid or amine in the liposome forming material in a molar ratio of between 1:20 and 1:0.05 relative to acid or amine and dispersing the mixture in an aqueous medium in a manner adequate to form liposomes. Alternatively, the hydrating agent liposome-forming material and the substance to be encapsulated can be added separately to the aqueous solution, then means for dispersion applied to form the liposomes.

SPECIFIC EMBODIMENTS

Definitions

For the purpose of this invention, a hydrating agent means a compound having at least two ionizable groups, preferably of opposite charge, one of which is capable of forming an easily dissociative ionic salt, which salt can complex with the ionic functionality of the acid or amine in the liposome-forming material. The hydrating agent inherently does not form liposomes in and of itself. Such agent will also be physiologically acceptable, i.e., it will not have any untoward or deleterious physiological effect on the host to which it is administered in the context of its use in this invention.

Complexing in this context denotes the formation of dissociative ionic salts where one functionality associates with the ionic functionality of the liposome-forming material and the other functionality has hydrophilic properties which impart water-solubility to the resulting complex.

Hydrate complex means the complex formed between the hydrating agent and the acid or amine in the liposome-forming material. Mixtures of the hydrating agent, liposome-forming materials and discrete amounts of water form a gel-like mass. When in this gel forms, the hydrating agent and acid or amine in conjunction with all liposome forming materials, arrange into a "hydrate complex" which is a highly ordered liquid crystal. While the liquid crystal structure varies with pH and amount of hydrating agent, the liquid crystal structure remains. NMR spectroscopy confirms that this crystal structure consists of multilamellar lipid bilayers and hydrophilic layers stacked together in alternating fashion. The $^{31}$P-NMR spectrum exhibits an anisotropic peak, confirming the existence of multilamellar bilayers.

The word "liposome" has been proposed and accepted as the term to be used in the scientific literature to describe synthetic, oligolamellar lipid vesicles. Such vesicles are usually comprised of one or more natural or synthetic lipid bilayers surrounding an internal aqueous phase.

Long chain aliphatic and/or aromatic-based acids or amines means acids or amines having an open chain structure and consisting of paraffin, olefin and acetylene hydrocarbons and their derivatives, i.e. saturated and unsaturated hydrocarbons or the backbone of such chain contians an where aromatic substituent. Such acids and amines may have more than one such function. Long chain means that the backbone of the aliphatic chain have ten or more carbon atoms. If the chain contains an aromatic group, such as phenyl, the chain will comprise at least a five carbon backbone in conjunction with that aromatic group. The chain of carbon atoms comprising the backbone may be variously substituted with saturated or unsaturated aliphatic or aromatic functions.

An acid or amine function is any such functionality. For example, an acid function may be a carboxylatic acid, or a phosphorus or sulfur derived acid function such as phosphate, phosphite or pyrophosphate or sulfate, sulfite, thiosulfate, or similarly constituted phosphorus or sulfur-based acid. Amines must be sufficiently basic so as to have an ionizable hydrogen or be capable of forming salts which have an ionization constant such that they are capable of forming the requisite hydrate complex described above.

The phrase "liposome-forming material" refers to all natural and synthetic compounds which have one ionizable function and a hydrophobic component, a fatty component, such as the phospholipids, non-volatile fatty acids, sulfates, sulfites, thiosulfates, or phosphates, non-volatile alkyl amines and the like which singly or in combination form liposomes when dispersed in an aqueous solution. This definition is not intended to be limiting in its scope but is to be read to include all compounds capable of forming lipid vesicles.

Examples of liposome-forming materials include saponifiable and non-saponifiable lipids, e.g., the acyl glycerols, the phosphoglycesides, sphingolipids, the glycolipids, etc. fatty acids include saturated or unsaturated alkyl ($C_8 \sim C_{24}$) carboxylic acids, mono-alkyl ($C_8 \sim C_{27}$) esters of $C_4 \sim C_{10}$ dicarboxylic acids (e.g., cholesterol hemi-succinic acid and fatty acid derivatives of amino acids in which any N-acyl carboxylic acids also are included (e.g., N-oleoyl threonine, N-linoleoyl serine, etc.). Mono- or di-alkyl ($C_8 \sim C_{24}$) sulfonate esters and mono- or di-alkyl ($C_8 \sim C_{24}$) phosphate esters can be substituted for the fatty acids. Furthermore, mono- or di-acyl ($C_8 \sim C_{24}$) glycerol derivatives of phosphoric acids and mono- or di-acyl ($C_8 \sim C_{24}$) glycerol derivatives of sulfuric acids can be used in place of the fatty acids.

Additionally, the fatty acids also can be replaced by amines (e.g., $C_8 \sim C_{24} NH_2$), $C_8 \sim C_{24}$ fatty acid derivatives of amines (e.g., $C_8 \sim C_{24} CONH \sim NH_2$), $C_8 \sim C_{24}$ fatty alcohol derivatives of amino acids (e.g., $C_8 \sim C_{24} OOC \sim NH_2$), and $C_8 \sim C_{24}$ fatty acid esters of amines (e.g., $C_8 \sim C_{24} COO \sim NH_2$).

Photopolymerizable lipids and/or fatty acids (or amines) (e.g., diacetylenic fatty acids) also can be included, which can provide a sealed liposome with cross-linked membrane bilayers upon photo-initiation of polymerization.

Although the primary components of these liposomes will be lipids, phospholipids, other fatty acids, there may also be added various other components to modify the liposomes' permeability. There may be added, for example, non-ionic lipid components such as polyoxy alcohol compounds, polyglycerol compounds or esters of polyols; the esters of polyols and synthetic lipolipids, such as cerebrosides. Other materials, such as long chain alcohols and diols, sterols, long chain amines and their quaternary ammonium derivatives; polyoxyethylenated fatty amines, esters of long chain amino alcohols and their salts and quaternary ammonium derivatives; phosphoric esters of fatty alcohols, polypeptides and proteins.

The composition of the liposome can be made of more than one component of the various kinds of lipids, the fatty acids, alkyl amines, or the like, and the hydrating agents.

It also has been discovered that if the lipid component itself or the substances (e.g., medicaments, biologically active compounds, cosmetics, etc.) to be encapsulated possess the aforementioned properties, the lipid composition may not require the inclusion of the fatty acids (or the amines) or the hydrating agents to form the "pre-liposome gel". For example, the mixture of dipalmitoylphosphatidylcholine (DPPC) and distearoyl phosphatidylethanolamine forms the "pre-liposome gel" or liposomes with aqueous glutamic acid solution and the mixture of DPPC and oleic acid with aqueous epinephrine solution forms the "pre-liposome gel" and liposomes.

For pharmaceutical application as a liposome drug delivery system, however, the composition of phospholipids, oleic acid (or phosphatidylethanolamine) and arginine or lysine (or glutamic acid and/or aspartic acid) are preferred.

When solids are referred to, the liposome-forming materials and its acid or amine component, hydrating agents, and material to be encapsulated if any, are what is being referred to.

Preferred Embodiments

The preferred hydrating agents of this invention are alpha amino acids having an ionizable omega substitution as a carboxylate, amino, and guanidino function and those compounds represented by the formula:

$$X-(CH_2)n-Y \qquad \qquad I$$

wherein

X is $H_2N-C(NH)-NH-$, $H_2N-$, $ZO_3S-$, or $ZO_2C-$ wherein Z is H or an inorganic or organic cation;

Y is $-CH(NH_2)-CO_2H$, $-NH_2$, $-NH-C(NH)-NH_2-COOH$, $CH(NH_2)SO_3Z$ or $ZH(NH_2)PO_3Z_2$ wherein Z is defined above; and n is the integer 1-10; or a pharmaceutically acceptable salt thereof. Also included in the list of preferred compounds are the N,N'-dialkyl substituted arginine compounds and similar compounds where the alkyl chain length is varied.

More preferred hydrating agents are the omega-substituted, alpha amino acids such as arginine, its N-acyl derivatives, homoarginine, gamma-aminobutyric acid, asparagine, lysine, ornithine, glutamic acid, aspartic acid or a compound represented by the following formulas:

$$H_2NC(NH)-NH-(CH_2)n-CH(NH_2)COOH \qquad II$$

$$H_2N-(CH_2)n-CH(NH_2)COOH \qquad III$$

$$H_2N-(CH_2)_n-NH_2 \qquad IV$$

$$H_2NC(NH)-NH-(CH_2)_n-NH-CH(NH)-NH_2 \qquad V$$

$$HOOC-(CH_2)_n-CH(NH_2)COOH \qquad VI$$

$$HOOC-(CH_2)_n-COOH \qquad \text{VII}$$

$$HO_3S-(CH_2)_n-CH(NH_2)COOH \qquad \text{VIII}$$

$$H_2O_3S-(CH_2)_n-CH(NH_2)COOH \qquad \text{IX}$$

$$HO_3S-(CH_2)_n-CH(NH_2)SO_3H \qquad \text{X}$$

$$H_2O_3S-(CH_2)_n-CH(NH)PO_3H_2 \qquad \text{XI}$$

wherein n is 2–4.

The most preferred compounds are arginine, homoarginine, gamma-aminobutyric acid, lysine, ornithine, glutamic acid or aspartic acid.

About 1:20 molar ratio of hydrating agent relative to the liposome-forming material will provide the salutory effects of this invention with an upper limit of about 1:0.05. The preferred concentration range for the hydrating agent is between a 1:2 to 1:0.5 molar ratio of the hydrating relative to the liposome-forming material.

The hydrating agents of this invention may be used alone or as a mixture. No limitation is implied or intended in the use of mixtures of these hydrating materials.

As a practical matter, thus a matter of preference, if liposomes are prepared with a long chain aliphatic or aromatic-based acid, it is preferred to use hydrating agents which contain at least one ionizable nitrogen, such as arginine, homoarginine, lysine, ornithine, and the like. Conversely, if the amphipatic materials used to form the liposomes contain a long chain aliphatic or aromatic-based amine, it is preferred to use a di-acid such as glutamic acid, aspartic acid; any of the alkyl di-acids such as the simple di-acids such as valeric acid, caprylic, caproic, capric or the like; or those di-acids having two phosphate, or sulfate functionalities; or those di-acids having mixed —COOH/—SO$_3$H or —COOH/—PO$_3$H$_2$ functions.

The hydrating agents of this invention are listed in the catalogue of many chemical producers, can be custom manufactured by such producers, or can be made by means known in the art.

Arginine, homoarginine, lysine, glutamic acid, aspartic acid, and other naturally occurring amino acids may be obtained by the hydrolysis of protein and separation of the individual amino acids or from bacterial sources.

The compounds of formula II can be made by the method of Eisele, K. et al, *Justusliebigs. Ann. Chem.*, p 2033 (1975). Further information on several representative examples of these compounds is available through their respective Chemical Abstracts Service numbers as follows: norarginine, CAS #14191-90-3; arginine, CAS #74-79-3; and homoarginine, CAS #151-86-5.

For representative examples of formula III, see for 2,4-diaminobutyric acid CAS #305-62-4 and for lysine CAS #56-87-1.

Methods for making representative compounds of formula IV are available from Chemical Abstracts as follows: ethane diamine, CAS #305-62-4; propane diamine—54618-94-9; and 1,4-diaminobutane, CAS #52165-57-8. See specifically Johnson, T. B., *J. Am. Chem. Soc.*, 38, 1854 (1916).

Of the compounds of formula VI, glutamic acid is well known in the art and is available from many commercial sources. How to make other representative compounds is contained in the literature, for example: 2-aminohexandioic acid—CAS #62787-49-9 and 2-aminoheptandioic acid—CAS #32224-51-0.

Glutamic acid, the compound of formula VII where n is 2 is well known in the art and can be made by the method of Maryel and Tuley, *Org. Syn.* 5, 69 (1925). Other representative compounds in this group can be made according to the art as referenced by the following CAS numbers: hexadioic acid, CAS #123-04-9 and heptadioic acid, CAS #111-16-0.

Homocysteic acid is known in the art referenced by CAS #56892-03-6. The compound 3-sulfovaline is described in the literature referenced by CAS #23405-34-2.

Certain aliphatic and aromatic-based acids and amines are preferred in the practice of this invention. Such compounds can have multiple functions such as having two or more acid or amine groups or combinations thereof. For example, one could use a di-acid, a di-amine or a compound having an acid and an amine function. The preferred compounds are those with one or two acid or amine functions. More preferred are the fatty mono-acids of 10–20 carbons, saturated and unsaturated. Most preferred are the alkyl and alkenyl acids of 10 to 20 carbon atoms, particularly oleic acid.

Gels

Mixtures of liposome-forming materials, a long chain aliphatic or aromatic-based acid or amine, and one or more hydrating agents with up to 300 moles of water relative to the total solids gives a gel which forms liposomes directly therefrom upon addition of an aqueous solution. This gel can be labeled a pre-liposome gel because i.) of its structural characteristics which are essentially those of liposomes and, ii.) the gel's facility for being converted into liposomes upon dilution with an aqueous solution. Aqueous solution in excess of about 300 moles cause the beginning of liposome formation.

The structure of this gel is a highly ordered liquid crystal which forms an optically clear solution. The X, Y, and Z dimensions of the liquid crystal vary with the concentrations of hydrating agent at the constant pH as well as with the pH of the solution. By varying the hydrating agent concentration at constant pH or changing the pH while maintaining percentage of hydrating agent, the size and number of lamellae structures of the lipid bilayers of the subsequent liposome vesicles can be controlled.

The gel structure itself can accommodate up to approximately 300 moles of water per mole of solid without disturbing the stability of the gel structure. The structure of the gel as determined by proton NMR spectroscopy is comprised of multilamellae lipid bilayers and hydrophillic layers stacked together in an alternating fashion. The $^{31}$P-NMR spectrum of the same gel exhibits an anisotropic peak further confirming that the gel consists of a multilamellar bilayer.

This gel can be autoclaved, a convenient means of sterilization Furthermore, the gel shows no discoloration and remains clear at room temperature for at least one year after being autoclaved. The gel can further be sterilized by filtration through an appropriate sterilization filter.

Upon dispersion of the gel into an aqueous solution, liposomes are efficiently and spontaneously produced.

The pre-liposome gel, with or without the material to be encapsulated, also can be dehydrated (e.g. lyophilized) and the powder rehydrated to form liposomes spontaneously, even after a long period of storage. This capability makes the invention particularly useful for administering water-sensitive medicaments where long term pre-use storage is needed.

Either water insoluble or water soluble chemicals, drugs, cosmetics, food materials and the like, can be incorporated into liposomes prepared using this material and by this method. Accordingly, the gel may be used as a delivery system for the administration of drugs via oral, parenteral, topical, intravenous, suppository routes or any other route of drug or chemical delivery. Here, a drug may be any substance that when taken into the living organism may modify one or more of its functions, for example as recited in an official pharmacopeia; or a substance used in the diagnosis, cure, mitigation, treatment or prevention of a disease.

The use of these liposomes is not limited to human or mammalian use but can be used in any industrial, agricultural, pharmaceutical, cosmetic or chemical application where lipid vesicle encapsulation and administration of compounds or materials is warranted or useful.

The versatility of the present invention is illustrated, but not limited, by the following examples.

EXAMPLE #1

Gel Preparation

Dipalmitoylphosphatidylcholine, 3.0 grams, was weighed into a 50 ml beaker. Oleic acid 1.2 grams was added and mixed together to form a uniform paste.

Arginine 0.72 grams in 30 ml of distilled deionized water was added to the dipalmitoylphosphatidylcholineoleic acid paste and heated to 45° C. With mixing by hand, the mixture formed a clear stable gel. The gel was stored and liposomes later formed by diluting the gel with phosphate buffered saline.

EXAMPLE #2

Preparation of Liposomes

Dipalmitoylphosphatidylcholine, 120 mg, and 24 mg of oleic acid were added together and mixed thoroughly until a white homogeneous paste was observed.

Then 20 mg of arginine was dissolved into 60 ml of phosphate buffered saline (ionic strength=0.15, pH=7.4). The arginine-saline solution was added to the paste and heated to 40° C. for ½ hour, or until a slightly turbid solution was observed.

EXAMPLE #3

Large Scale Gel and Liposome Preparation i). Gel Manufacture: To 50 grams of egg phosphatide powder type 20 (Ashai ChemicalS) was added 20 grams of oleic acid N.F. Mixing gave a white paste which was cooled to 4° C. and ground into a fine powder. This powder was added to an aqueous solution containing 20 grams of arginine and 500 grams of distilled deionized water. The mixture was mixed with a spatula as the solution was heated to about 35° C. to help hydrate phospholipids. A homogeneous, slightly yellow gel was formed. This gel can be stored at 4° C. or can be frozen and later reconstituted.

ii). Manufacture of Liposomes: The gel prepared in the preceding Paragraph was taken from cold storage and returned to room temperature. It was then mixed with 2 liters of phosphate buffered saline, pH 7.4. A white opaque liposome solution was formed.

EXAMPLE #4

Liposome Formation from the Gel

A homogeneous paste of 1.0 gram of dipalmitoylphosphatidylcholine (DPPC) and 400 mg of oleic acid was formed. Then 300 mg of arginine was mixed in 10 ml of phosphate buffered saline, heated to 45° C. and added to the DPPC/oleic acid paste to form liposomes.

EXAMPLE #5

Pre-Liposome Gel

One gram of dipalmitoylphosphatidylcholine (DPPL) was mixed with 400 mg of oleic acid to form a homogeneous paste. 300 mg of arginine was mixed with 2 ml of water at 45° C. until dissolved. The arginine solution was mixed with the DPPC/oleic acid paste at about 45° C. to give a thick gel. Liposomes formed when this gel was diluted with phosphate buffered saline.

EXAMPLE #6

Cholesterol Containing Liposomes

Cholesterol, 15 mg, was mixed with 100 mg dipalmitoylphosphatidylcholine (DPPC) to form a homogeneous powder. Then 23 mg of oleic acid was added to the powder and thoroughly mixed to form a homogeneous paste. To make liposomes, 30 mg of arginine was added to 10 ml of phosphate buffered saline, heated to 40° C. and added to the DPPC/cholesterol/oleic acid paste. The combination was mixed at 40° C. to obtain liposomes.

EXAMPLE #7

Palmitic Acid-Containing Liposomes

Dipalmitoylphosphatidylcholine (DPPC) 250 mg was mixed with 25 mg of palmitic acid to form a uniform powder. Then 80 mg of oleic acid was mixed with this powder and heated to 45° C. with constant stirring until a uniform paste was formed. Arginine 100 mg was dissolved in 25 ml of distilled deionized water and heated to 45° C. This arginine solution was added to the paste at 45° C. and mixed until a uniform homogeneous gel was formed. The gel was diluted ten fold with phosphate buffered saline to form liposomes.

EXAMPLE #8

Isostearic Acid-Containing Liposomes

Dipalmitoylphosphatidylcholine 100 mg was mixed with 50 mg of isostearic acid to form a uniform homogeneous paste. An arginine solution of 50 mg of arginine in 2.0 ml of distilled deionized water was made and added to the isostearic acid paste and heated to 45° C. The mixture was mixed until a clear gel was formed. Liposomes are formed upon dilution with phosphate-buffered saline.

EXAMPLE #9

Oleoyl Threonine Containing Liposomes

Dipalmitoylphosphatidylcholine 125 mg and 75 mg of oleoyl threonine were added together and heated to 40° C. to form a paste. Then 2 ml of distilled deionized water was added with constant mixing at 40° C. A clear gel was formed which can be diluted with phosphate buffer saline at pH 5 to form liposomes.

EXAMPLE #10

Myristyl Amine Containing Liposomes

Dipalmitoylphosphatidylcholine 192 mg was added to 72 mg of myristyl amine and heated with constant mixing until a uniform paste was formed. Glutamic acid 65 mg in 5 ml of distilled deionized water was added to the paste and heated until a gel was formed. Phosphate buffered saline was added to the gel to form liposomes.

Example #11

DLPC Containing Liposomes

Dilaurylphosphatidylcholine (DLPC) 50 mg was mixed with 20 mg oleic acid to form a homogeneous paste. Arginine 20 mg was added to 10 ml of phosphate buffered saline, added to the paste and hand mixed until a turbid liposome solution formed.

Example #12

Phosphatidylethanolamine-Glutamic Acid Liposomes

L-glutamic acid 32 mg was dissolved in 2.0 ml of distilled deionized water and the pH adjusted to 5.2 with 1.0N sodium hydroxide. This solution was heated to 60° C., and 100 mg of phosphatidylethanolamine added. The solution was kept at 60° C. with constant mixing until a uniform viscous gel was observed.

The phosphatidylethanolamine-glutamic acid gel was diluted 1/10 by phosphate buffered saline. Vesicular like structures are observed under phase contrast light microscopy.

EXAMPLE #13

Dipivalyleoinephrine Liposomes

One gram of dipalmitoylphosphatidylcholine was mixed with 396 mg of oleic acid, until a homogeneous paste formed. Then 400 mg of arginine in 20 ml of distilled deionized water was added to form a pre-vesicle clear gel.

To make the liposomes, 242 mg of dipivalylepinephrine was dissolved in 10 ml of distilled deionized water. Then 5 grams of the pre-vesicle gel was mixed with 5 grams of the dipivalylepinephrine solution after which 50 ml of phosphate buffered saline was added forming a liposome solution.

EXAMPLE #14

Flurbiprofen Liposomes

To make these liposomes, 980 mg of dipalmitoylphosphatidylcholine, 370 mg of oleic acid, and 320 mg of flurbiprofen (free acid) were mixed together until a homogeneous paste was observed. Then 510 mg of arginine in 10 ml of purified water was added to the paste and heated to 41° C. with constant mixing for 30 minutes. A clear pre-vesicle gel formed of which 5 grams was introduced into 50 ml of phosphate buffered saline and mixed with a stir bar until a bluish translucent solution was observed.

EXAMPLE #15

Levobunolol Liposomes

Thirty mg of dipalmitoylphosphatidylcholine and 15 mg of cholesterol were weighed into a 4 ml vial. Ten mg of linoleic acid was added and mixed together to form a uniform paste. Two ml of a 1% aqueous levobunolol solution containing 10 mg of arginine was added to the paste and mixed together. Then 10 ml of phosphate buffer solution was added and heated to 45° C. to form liposomes.

EXAMPLE #16

Pilocarpine Liposomes

To 120 mg of dipalmitoylphosphatidylcholine was added 40 mg of oleic acid to form a homogeneous paste. Forty mg of pilocarpine free base was added to 10 ml of distilled deionized water. This solution was added to the paste and heated to 45° C. to form a pre-liposome gel. The resulting gel was diluted with 20 ml of phosphate buffered saline to form liposomes.

EXAMPLE #17

Epinephrine Liposomes

Dipalmitoylphosphatidylcholine 250 mg was mixed with 100 mg of oleic acid to form a homogeneous paste. 50 mg of epinephrine, free base, was dissolved in 5.0 ml of distilled deionized water, heated to 40° C. and added to the dipalmitoylphosphatidylcholine/oleic acid paste. This solution was mixed until a homogeneous viscous creamy gel was observed. This gel was diluted 1/5 with phosphate buffered saline (pH 7.22) to form liposomes.

EXAMPLE #18

Effect of Arginine Concentration on Liposome Size

To 502 mg of dipalmitoylphosphatidylcholine (DPPC) was added 10 microliters of (2-palmitoyl-1-$C^{14}$) (0.1 mCi/ml) dipalmitoylphosphatidylcholine. Chloroform was added to effect complete mixing of the radioactivity and then evaporated. Oleic acid (OA), 195 mg, was then mixed into the lipid to form a paste. Five ml of distilled water containing 119 mg of arginine was added and mixed at 45° C. to form a clear gel.

One gram of the gel was weighed into four different vials and arginine was added as follows:

| Sample ID | Sample Composition DPPC:OA:Arg |
|---|---|
| Vial 1 + 1 ml water | (1:1:1) |
| Vial 2 + 1 ml of 50 mg/ml Arg in H₂O | (1:1:3) |
| Vial 3 + 1 ml of 84 mg/ml Arg in H₂O | (1:1:5) |
| Vial 4 + 1 ml of 192 mg/ml Arg in H₂O | (1:1:10) |

One-half gram of each solution was diluted in 50 ml phosphate buffered saline of pH 7.8.

The estimated weight diameter was obtained from a Sephracyl S-1000 column chromatographic analysis employing $^{14}C$-isotope labelled DPPC. The effects are given in the following Table.

TABLE II

Effects of Arginine Concentration on Vesicle Size

| System | pH | Estimated Weight Diameter (nm) |
|---|---|---|
| DPPC:OA:Arg (1:1:1) | 7.8 | ~220 |
| DPPC:OA:Arg (1:1:3) | 7.8 | ~140 |
| DPPC:OA:Arg (1:1:5) | 7.8 | ~90 |
| DPPC:OA:Arg (1:1:10) | 7.8 | ~20 |

EXAMPLE #19 pH Effect on Vesicle Size

Additionally, the vesicle size can be varied by varying the pH of the aqueous buffer solution.

To 100 mg of dipalmitoylphosphatidylcholine (DPPC) was added 25 microliters of (2-palmitoyl-1-$C^{14}$) (0.1 mCi/ml) dipalmitoylphosphatidylcholine. Chloroform was added to effect complete mixing of the radioactivity and then evaporated. Oleic acid (OA), 40.1 mg, was then mixed into the lipid to form a paste. One ml of a solution containing 24 mg/ml arginine in water was added to the lipid mixture and mixed at 45° C. to form a clear gel.

Two 100 mg aliquots of this gel were diluted in 10 ml of phosphate buffer at pH 9.0 and 7.4 respectively.

Again, the estimated weight diameter (A) was obtained from the Sephracyl S-1000 column chromatographic analysis employing $^{14}C$—isotope labelled dipalmitoylphosphotidylcholine. Results are given in the following Table.

TABLE III

| pH Effects on Vesicle Size | | |
|---|---|---|
| | | Estimated Weight |
| System | pH | Diameter (nm) |
| DPPC:OA:Arg (1:1:1) | 7.4 | ~>300 |
| DPPC:OA:Arg (1:1:1) | 7.8 | ~220 |
| DPPC:OA:Arg (1:1:1) | 9.0 | ~25.4 |

Thus, a desired size of the liposomal vesicles can be prepared by varying the arginine concentration or the pH of the aqueous buffer solution.

EXAMPLE #20

Liposome Stability

Sterile liposomes may be prepared from the heat sterilized pre-liposome gel. Alternatively, the liposome gel or the liposomes may be sterile filtered through an appropriate sterilizing filter.

Liposomes prepared from DPPC:OA:Arg (1:1:2) at pH 8.0 were heat sterilized and stored at room temperature for approximately one year without adding antimicrobial agents and anti-oxidants. No bacterial growth, discoloration and precipitation were observed. Negative stain electron microscopic examination of the one year old liposomes revealed that the liposomal vesicles are stable.

EXAMPLE #21

Encapsulated sucrose latency was measured using $C^{14}$-sucrose encapsulated with the DPPC:OA:Arg (1:1:1) liposome system in aqueous Phosphate buffer solution at pH 7.8. The result was Presented in Table IV.

TABLE IV

| % Sucrose Latency | |
|---|---|
| Days | % Latency |
| 0 | 100 |
| 1 | 97.4 |
| 3 | 93.4 |
| 7 | 91.4 |

Thus, the present liposome system has an excellent latency for drug delivery.

EXAMPLE #22

Efficiency of Encapsulation

A number of drugs were encapsulated with 10 mg/ml DPPC:oleic acid:Arg (1:1:1) liposomes to illustrate medicament encapsulation for use as a drug delivery system. The results are presented in Table V.

TABLE V

| | Entrapment of Drugs | |
|---|---|---|
| Drugs | pH | % Entrapment |
| Flurbiprofen | 7.8 PBS | 90% |
| Dipivalyl Epinephrine | 7.1 PBS | 80% |

EXAMPLE #23

Lyophilized Liposomes

Oleic acid, 30.0 gm, and 7.5 gm of cholesterol U.S.P. were confected. Then 75.0 gm of phosphatide type 20 powder (Asahi Chemical Co.) was mixed with the oleic acid/cholesterol mixture until an homogeneous paste was formed.

Then 15.0 gm of arginine (free base) was dissolved in 183 gm of distilled, deionized water. This arginine solution was mixed slowly with the lipid paste to form a homogeneous gel. The gel PH was adjusted to 7.4 using 5.0N HCl.

A 10.0 gm aliquot of this pre-liposome gel was transferred to a 10 ml vial and lyophilized. The resulting powder formed liposomes when diluted with 5 ml of phosphate buffered saline.

EXAMPLE 24

Indomethacin Absorption from Gels

The bioavailibility of indomethacin in a gel formulation was compared with that of a suspenison of indomethacin, both being compared with an IV dose. Rats were dosed with 5 mg/Kg of indomethacin. Oleic acid, arginine and phosphatide #5 (described above) in the a the the ratio 1:1:1 was used to make the gel. The suspension comprised indomethacin in 1.0% Methocel (weight/volume) in water. Blood levels were measured 0–30 hours. Summarized data is as follows:

| Formulation | AUC | Peak | C Max |
|---|---|---|---|
| Suspension | 56 ± 15% | 60 Min | 12.2 ± 2.4 µg/ml |
| Gel | 112 ± 35% | 240 Min. | 19.8 ± 7.8 µg/ml |

At time equals 0, the IV dose showed concentration of 117 micrograms/ml. Increased bioavailability with the gel is demonstrated by this data, plus delayed absorption.

What is claimed is:

1. An improved composition for making liposomes said improved composition being in the form of an aqueous gel comprising:
   a. liposome-forming material containing a long chain aliphatic or aromatic-based acid or amine;
   b. a hydrating agent of charge opposite to that of the acid or amine, which agent is present in a molar ratio of between 1:20 and 1:0.05 relative to the acid or amine and wherein said hydrating agent is a carboxylate, amino, or guanidino function or a pharmaceutically acceptable salt thereof, or a compound of the formula:

$$X—(CH_2)_n—Y \qquad I$$

wherein

X is $H_2N—C(NH)—NH—$, $H_2N—$, $ZO_3S—$, $Z_2O_3P—$, or $ZO_2C—$ wherein Z is H or an inorganic or organic cation;

Y is $—CH(NH_2)—CO_2H$, $—NH_2$, $—NH—C(NH)—NH_2—COOH$, $CH(NH_2)SO_3Z$ or $ZH(NH_2)PO_3Z_2$ wherein Z is defined above; and n is the integer 1–10; or a pharmaceutically acceptable salt thereof and the acid or amine is an alkyl or alkenyl acid or amine of 10 to 20 carbon atoms; and c. water in an amount up to 300 moles relative to the solids.

2. The composition of claim 1 wherein said hydrating agent is arginine, homoarginine, or their N-acyl derivatives, gamma-aminobutyric acid, asparagine, lysine, ornithine, glutamic acid, aspartic acid or a compound of the formula:

$$H_2NC(NH)—NH—(CH_2)_n—CH(NH_2)COOH \qquad II$$

$$H_2N—(CH_2)_n—CH(NH_2)COOH \qquad III$$

$$H_2N—(CH_2)_n—NH_2 \qquad IV$$

$$H_2NC(NH)—NH—(CH_2)_n—NH—CH(NH)—NH_2 \qquad V$$

$$HOOC—(CH_2)_n—CH(NH_2)COOH \qquad VI$$

$$HO_3S—(CH_2)_n—CH(NH_2)COOH \qquad VII$$

$$H_2O_3S—(CH_2)_n—CH(NH_2)COOH \qquad VIII$$

$$HO_3S—(CH_2)_n—CH(NH_2)SO_3H \qquad IX,$$

or $$H_2O_3S—(CH_2)_n—CH(NH)PO_3H_2 \qquad X$$

wherein n is 2–4, or a pharmaceutically acceptable salt thereof.

3. The composition of claim 2 wherein the hydrating agent is present in an amount between 1:2 to 1:0.5 molar ratio relative to the liposome-forming material.

4. The composition of claim 3 wherein said hydrating agent is arginine, homoarginine, gamma-aminobutyric acid, lysine, or ornithine, or a pharmaceutically acceptable salt thereof.

5. The composition of claim 3 wherein said hydrating agent is glutamic acid or aspartic acid or a pharmaceutically acceptable salt thereof.

6. A composition according to claim 1 which contains a drug.

7. A composition according to claim 6 for oral or intravenous administration of a drug.

8. An improved method for preparing liposomes, which improved method comprises preparing without the use of an organic solvent an aqueous gel comprising:

a) liposome-forming material containing a long chain aliphatic or aromatic-based acid or amine;

b) a hydrating agent of charge opposite to that of the acid or amine, which agent is present in a molar ratio of between 1:20 and 1:0.05 relative to the acid or amine and wherein said hydrating agent is a carboxylate, amino, or guanidino function or a pharmaceutically acceptable salt thereof, or a compound of the formula:

$$X—(CH_2)_n—Y \qquad I$$

wherein

X is $H_2N—C(NH)—NH—$, $H_2N—$, $ZO_3S—$, $Z_2O_3P—$, or $ZO_2C—$ wherein Z is H or an inorganic or organic cation;

Y is $—CH(NH_2)—CO_2H$, $—NH_2$, $—NH—C(NH)—NH_2—COOH$, $CH(NH_2)SO_3Z$ or $ZH(NH_2)PO_3Z_2$ wherein Z is defined above; and n is the integer 1–10; or a pharmaceutically acceptable salt thereof and the acid or amine is an alkyl or alkenyl acid or amine of 10 to 20 carbon atoms; and c. water in an amount up to 300 moles relative to the solids; and dispersing said gel in an aqueous solution in a manner adequate to form liposomes.

9. The method of claim 8 wherein the hydrating agent is present in an amount between 1:2 and 1:0.05 molar ratio relative to the liposome-forming material.

10. The method of claim 9 wherein said hydrating agent is arginine, homoarginine, or their N-acyl derivatives, gamma-aminobutyric acid, asparagine, lysine, ornithine, glutamic acid, aspartic acid or a compound of the formula:

$$H_2NC(NH)—NH—(CH_2)_n—CH(NH_2)COOH \qquad II$$

$$H_2N—(CH_2)_n—CH(NH_2)COOH \qquad III$$

$$H_2N—(CH_2)_n—NH_2 \qquad IV$$

$$H_2NC(NH)—NH—(CH_2)_n—NH—CH(NH)—NH_2 \qquad V$$

$$HOOC—(CH_2)_n—CH(NH_2)COOH \qquad VI$$

$$HOOC—(CH_2)_n—COOH \qquad VI$$

$$HO_3S—(CH_2)_n—CH(NH_2)COOH \qquad VII$$

$$H_2O_3S—(CH_2)_n—CH(NH_2)COOH \qquad VIII$$

$$HO_3S—(CH_2)_n—CH(NH_2)SO_3H \qquad IX,$$

or $$H_2O_3S—(CH_2)_n—CH(NH_2)PO_3H_2 \qquad X$$

wherein n is 2–4, or a pharmaceutically acceptable salt thereof.

11. The method of claim 10 where said hydrating agent is glutamic acid or aspartic acid or a pharmaceutically acceptable salt thereof.

* * * * *